United States Patent [19]

Doleman et al.

[11] Patent Number: 5,015,445

[45] Date of Patent: May 14, 1991

[54] PROCESS AND APPARATUS FOR HYDROLYSIS OF PROTEINS AND PEPTIDES

[75] Inventors: Muriel S. Doleman; Patricia Webber, both of Wilmington, Del.

[73] Assignee: E. I. du Pont de Nemours and Company, Wilmington, Del.

[21] Appl. No.: 283,531

[22] Filed: Dec. 12, 1988

[51] Int. Cl.⁵ .......................................... F28D 21/00
[52] U.S. Cl. ................................. 422/204; 422/102; 204/157.68
[58] Field of Search ....................... 435/173, 296, 312; 204/157.68; 422/102, 104; 206/564; 494/33

[56] References Cited

U.S. PATENT DOCUMENTS

| | | | |
|---|---|---|---|
| 3,948,733 | 4/1976 | Conkerton | 435/296 |
| 4,140,489 | 2/1979 | Lee | 435/296 |
| 4,246,352 | 1/1981 | Budemeyer | 435/296 |
| 4,258,630 | 3/1981 | Jorgenson et al. | 108/20 |
| 4,456,805 | 6/1984 | Jorgensen et al. | 219/10.55 F |
| 4,504,715 | 3/1985 | Jorgensen et al. | 219/10.55 F |

OTHER PUBLICATIONS

Hirs etal., J. Biol. Chem., 211: 941–950 (1954).
Tsugita et al., Eur. J. Biochem., vol. 124, pp. 585–588 (1982).
Westall et al., Analyt. Biochem., vol. 61, pp. 610–613 (1974).
Chen et al., Int. J. Peptide Protein Res., vol. 30, pp. 572–576 (1987).
Kingston et al., Anal. Chem., 58, 2534–2544 (1986).
Fernando et al., Anal. Chem., 58, 511–512 (1986).
Fischer, Anal. Chem., 58, 261–263 (1986).
Westall et al., J. Org. Chem., No.21 (1972).

Primary Examiner—John F. Niebling
Assistant Examiner—Kathryn Gorgos

[57] ABSTRACT

This invention relates to a process and apparatus for producing constitutent amino acids from proteins and peptides and, in particular, for rapid microwave hydrolysis of proteins and peptides for amino acid analysis.

4 Claims, 2 Drawing Sheets

PROCESS AND APPARATUS FOR HYDROLYSIS OF PROTEINS AND PEPTIDES

BACKGROUND OF THE INVENTION

1. Field of the Invention

This invention relates to a method and apparatus for rapidly producing constituent amino acids from proteins and peptides and, in particular, for microwave hydrolysis of proteins and peptides for amino acid analysis.

2. Description of the Related Art

There is a great need in modern biology to understand and explain the physical structure of proteins and peptides. A protein is a complex union of amino acids. A peptide is a combination of amino acids formed by the linkage of amino groups of some amino acids with carboxyl groups of other amino acids. For the purpose of this disclosure, the term "protein(s)" is intended and defined to include peptide(s).

One way to learn about proteins is to break apart or reduce the proteins to their constituent amino acids and then analyze the resulting amino acids. Proteins can be broken apart by hydrolyzing them. That is, proteins are caused to react with water such that parts of the proteins combine with a hydrogen ion ($H_+$) and other parts of the protein combine with an hydroxyl anion ($OH_-$) to form the constituent amino acids of the proteins.

Hirs et al. discloses the hydrolysis of proteins by heating them in sealed glass tubes with 6 N hydrochloric acid at a temperature of about 110 degrees Celcius (° C). See Hirs et al., J. Biol. Chem., 211:941–950 (1954). This process requires between 16 and 24 hours for complete hydrolysis to occur depending on the protein, since some proteins are more difficult to hydrolyze than others. Complete hydrolysis of the protein sample is necessary to fully analyze the resulting amino acids. After hydrolysis, the tube is cooled, opened and the acid evaporated forming a solid comprising the constituent amino acids of the protein. Then the solid is dissolved in a buffer solution resulting in a mixture called a hydrolysate. Analysis of a hydrolysate on a modern amino acid analyzer takes from 30 minutes to 60 minutes depending on the analyzer. The most significant rate-limiting step in obtaining amino acid data from a protein sample is, thus, the hydrolysis procedure.

Various protein hydrolysis methods have been published using mixed hydrochloric and trifluoroacetic acids (see Tsugita et al., Eur. J. Volume 124, pages 585–588, 1982) and mixed and proprionic acids (see Westall et al., Analyt. Biochem., Volume 61, pages 610–613, 1974). These methods have not resluted in widespread use.

Shui-Tein Chen et al. in "Rapid Hydrolysis of Proteins and Peptides by Means of Microwave Technology and its Application to Amino Acid Analysis", Int. J. Peptide Protein Res., Volume 30, pages 572–576, 1987 disclose that proteins were hydrolyzed in a specifically constructed Teflon ®vial by heating the sample in a microwave oven. Chen et al. tried to hydrolyze proteins in Pyrex ®glass tubes with 6 N hydrochloric acid but an explosion of the reaction tubes resulted inside the microwave oven due to the high pressure and temperature induced in the sealed tubes.

There is a disadvantage to hydrolyzing proteins in a Teflon ®vial as disclosed in Chen et al. It is much harder to remove the resulting amino acids from a Teflon ®vial than a glass one. In fact, amino acids migrate into the Teflon ®vial during hydrolysis. Whereas, they don't migrate into glass during hydrolysis. This migration effect becomes more significant the smaller the sample of proteins being hydrolyzed and the larger the interior surface area of the vial.

Chen et al. disclosed hydrolysis of native ribonuclease A, oxidized ribonuclease A, and insulin B after exposing them to about 560 watts of microwave energy for 1 to 7 minutes. There are many proteins that are harder to hydrolyze than those proteins. Further, the constituent amino acids of the proteins hydrolyzed by Chen et al. do not include methionine, one of the most labile (or unstable) amino acids. Chen et al. do not disclose the specific amounts of proteins used or the percent of the hydrolyzed proteins that they recovered in the analysis.

Chen et al. discloses using vials with a volume of 2 milliliters (mL). Tsugita et al., supra., disclose hydrolyzing samples in 0.05 to 3.00 milliliters of total solution volume.

Clearly if a process and apparatus could be developed that significantly reduced the hydrolysis time of proteins, it would greatly facilitate amino acid analysis and, thus, the understanding of proteins.

An object of this invention is to provide a reliable reproducible process and apparatus for rapid hydrolysis of proteins for amino acid analysis.

Another object of this invention is to provide a reliable reproducible process and apparatus for rapid hydrolysis of microgram quantities of proteins.

Another object of this invention is to provide a reliable reproducible process and apparatus for rapid hydrolysis of proteins with greater than 60% recovery of the constituent amino acids including labile amino acids, such as serine, methionine and threonine.

SUMMARY OF THE INVENTION

This invention fulfills the above objectives through an apparatus for holding a sample of proteins dissolved in an aqueous acidic solution while the sample is being exposed to microwaves hydrolyzing the proteins, the apparatus comprising:

a replaceable tube including a nonpyrolyzable glass body enclosing an inner space for holding proteins dissolved in a solution, the body having a substantially flat surface with an opening to the inner space;

a holder including a body having an outer threaded portion ending with a lip, an inner chamber defined by an inner wall substantially the shape of and for holding the tube, and a substantially flat surface connected to the lip, the substantially flat holder surface having a hole leading to the holder inner chamber, such that the tube can be inserted into the hole until the tube rests on the inner chamber wall and the substantially flat tube surface is substantially parallel to and slightly extended from the substantially flat holder surface;

a disk-shaped septum having a side for contacting the substantially flat surfaces of the tube and the holder such that when the side of the disk is contacting the substantially flat tube and holder surfaces, the disk extends slightly beyond the lip; and a cap including an inner threaded portion connected to an inner wall, such that the inner threaded portion of the cap screws onto the outer threaded portion of the holder compressing the septum between the cap inner wall and the substantially flat tube and holder surfaces sealing the apparatus when holding a sample of proteins dissolved in an aqueous acidic solution while the sample is being exposed to microwaves to hydrolyze the proteins.

The invention can also be described as a process of producing constituent amino acids from proteins and/or peptides comprising the step of:

heating by exposing to microwaves a sample of proteins and/or peptides dissolved in an aqueous acidic solution in a replaceable nonpyrolyzable tube sealed with a septum within a holder and a cap.

DETAILED DESCRIPTION OF THE INVENTION

The present invention comprises a process and an apparatus for hydrolysis of proteins.

Figure 1:
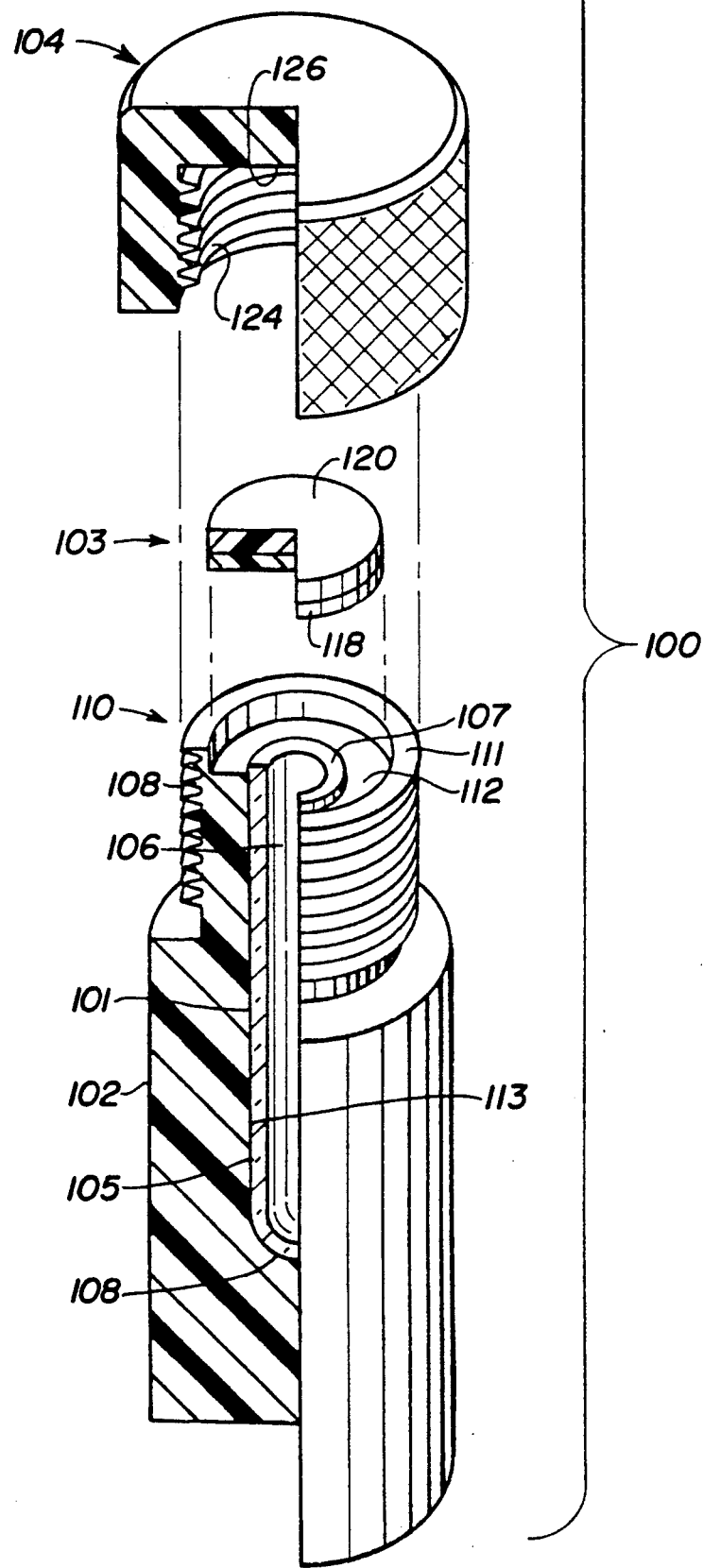
FIG. 1 is a tube holder apparatus for hydrolysis of proteins.

Referring to FIG. 1, there is illustrated an apparatus 100 for hydrolysis of proteins in accordance with the present invention. The apparatus 100 comprises a container or tube 101, a tube holder 102, a septum 103, and a cap or closure 104.

The tube 101 includes a body 105 that encloses an inner space 106 for holding protein dissolved in an aqueous acidic solution. The inner space 106 of tube 101 can contain up to and no more than 0.5 milliliters (mL) of sample. Thus, the volume of tube 101 is limited to a maximum of 0.5 milliliters (mL). The body 105 has a substantially flat edge or surface 107 with an opening to the inner space. The tube also has a closed end. The tube 101 may, for instance, be the shape of a common test tube. Preferably, the tube 101 is free from organic compounds or nonpyrolyzable which is defined as a tube that will withstand temperatures (e.g., 400° C. or higher) that will pyrolyze or convert to carbon dioxide any carbonaceous material. The tube can be made of Pyrex ®glass.

The tube holder 102 includes a body having an outer threaded portion 108. The threaded portion 108 has machine threads which do not taper from one end of the portion 108 to the other end. The threaded portion 108 ends in a lip 110 that includes a first substantially flat annular surface or edge 111. Adjacent and connected to the lip 110 recessed in from the first substantially flat annular surface or edge 111 is a second substantially flat annular surface or edge 112. The second substantially flat annular surface or edge 112 surrounds a hole or opening into an inner chamber defined by a wall 113. The inner chamber wall 113 is substantially the shape of the outer surface of the tube 101 such that the closed end of the tube can be inserted into the hole until the outer surface of the tube 101 substantially rests or is substantially supported by the inner chamber wall 113. When fully inserted like this, the substantially flat surface or edge 107 of the tube 101 is substantially parallel to and extends between the substantially flat surface or edges 111 and 112 of the holder 102.

The tube 101 is removeable from the holder 102. Therefore, the tube 101 is replaceable, disposable and provides for reuse of the holder 102 and cap 104.

The septum 103 is disk-shaped and sized such that when one of the flat sides of the septum is set on the holder second surface or edge 112, then the septum 103 will substantially fill the space between the second surface 112 and the holder first surface or edge 111. Further, the septum 103 has a thickness such that when it properly rests on the second surface or edge 112 without a tube 101 in the holder 102, then the septum 103 extends slightly farther away from the second surface or edge 112 than the first surface or edge 111 does.

Preferably, the septum 103 is a self-sealing septum 103 such as available from Walters Associates, Milford, MA. 10757. This septum 103 comprises a lower Teflon ®disk layer 118 connected to an upper silicon disk layer 120.

The cap or closure 104 comprises an inner threaded portion 124 connected to an inner wall 126, such that the inner threaded portion 124 screws onto the outer threaded portion 108 of the holder. When the tube 101 is inserted in the holder 102, the septum 103 is set on the holder second surface 112, and the outer threaded portion 108, then the septum 103 is compressed between the cap inner wall 126, the substantially flat tube surface or edge 107 and the second substantially flat holder surface or edge 112. Preferably, the outer threaded portion 108 is longer than the inner threaded portion 124 to enable the cap 104 to be screwed onto the holder very tightly.

The aforesaid apparatus 100 is capable of holding a sample of proteins dissolved in an aqueous acidic solution while the sample is being exposed to microwaves hydrolyzing the proteins. More specifically, the apparatus 100 can maintain a sample of proteins sealed within it during complete hydrolysis when the sample is heated by exposure to microwaves.

Figure 2:
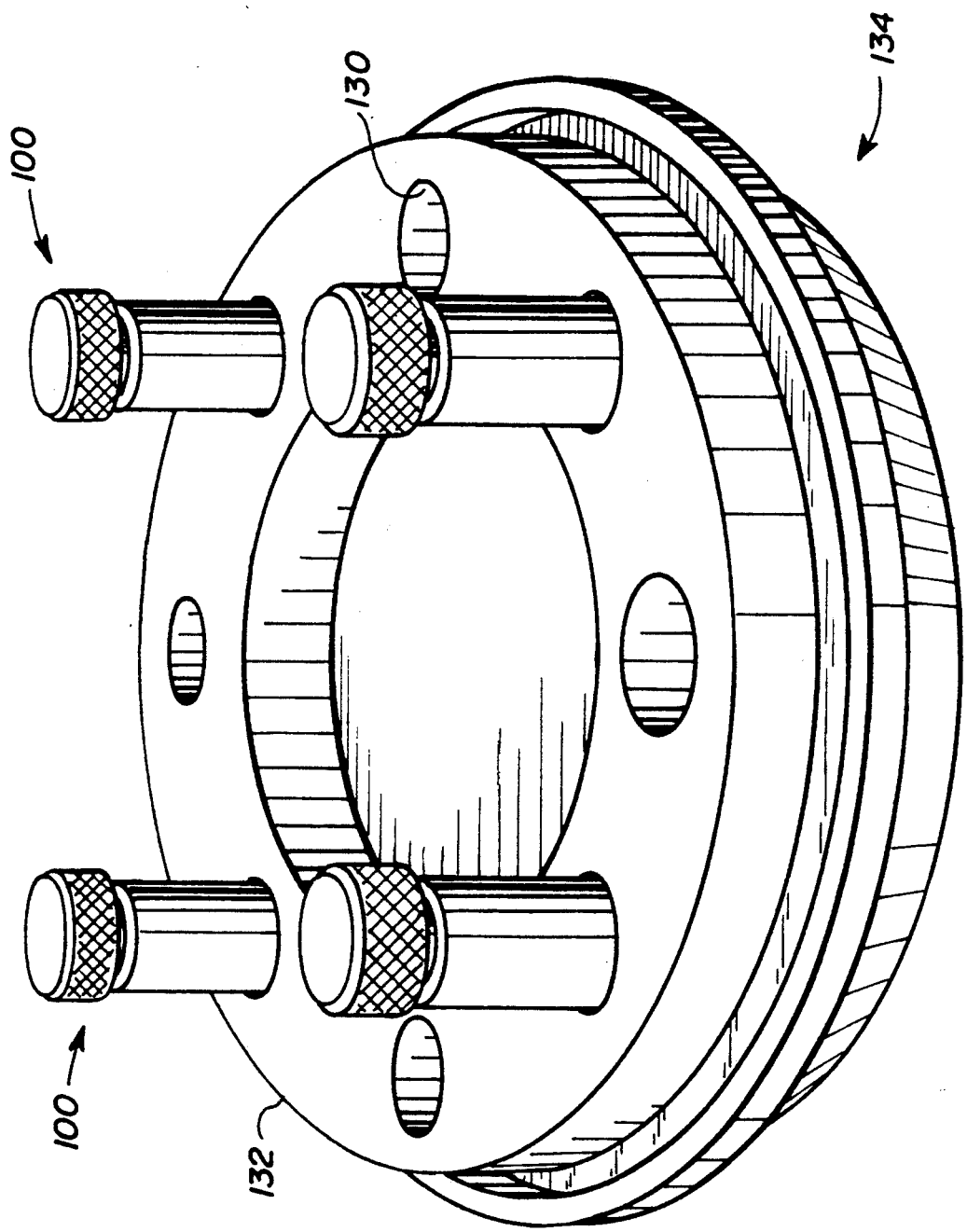
FIG. 2 is a slowly rotating apparatus which includes a plurality of tube holders.

Referring to FIG. 2, the apparatus of the present invention can include a plurality of the aforesaid apparatuses 100, an apparatus support 132 and a device 134 for slowly rotating the support 132 and the apparatuses 100 to provide even heating or exposure to the microwaves of the samples in a microwave oven.

The rotatable device 134 can be any means for slowly rotating the support 132 and the apparatuses 100. Suitable examples of such devices are disclosed in U.S. Pat. Nos. 4,258,630; 4,456,855 and 4,504,715.

The apparatus support 132 can be any shape and material as long as it can hold the plurality of apparatuses 100 substantially evenly spaced in a microwave oven. If the rotatable device 134 is weight activated, like those described in U.S. Pat. Nos. 5,258,630; 4,456,855 and 4,504,715, then the weight of the support 132 and the apparatuses 100 must be sufficient to cause the device 134 to rotate. The support 132 can be made of a body shaped like a disk, a ring (as illustrated), a hub with spokes, or any other shape that will cause the apparatuses 100 to be substantially evenly exposed in a microwave oven. The illustrated ring shaped support 132 has a plurality of holes 130 for inserting a plurality of the holders 102. Any number of holes 130 is possible as long as the samples are substantially evenly distributed on the rotatable device 134 for even heating in a microwave oven.

The holder 102, the cap 104 and the support 132 can be made of any material that can be used in a microwave oven and withstand the temperatures and pressures contemplated herein. They can comprise a polymeric material, such as a fluorocarbon resin. Preferably, they comprise a copolymer of tetrafluoroethylene and hexafluoropropylene, such as Teflon ®.

The present invention further comprises a process for hydrolysis of proteins or for producing constituent amino acids from proteins comprising the step of heating by exposing to microwaves a sample of proteins dissolved in an aqueous acidic solution in the replaceable nonpyrolyzable tube 101 sealed with the septum 103 within the holder 102 and a cap 104.

The proteins dissolved in an aqueous acidic solution can be prepared as follows.

First, the tube 101 is pyrolyzed and a dry sample of proteins is obtained, dried (if necessary) and located in the pyrolyzed tube 101. If the sample is originally dry, it can be placed in the tube 101 before or after the tube is placed in the holder 102.

If the proteins are originally in an aqueous solution, then the sample is put in a tube, such as the tube 101, and then dried by evaporation to a solid by any suitable means, such as, by means of a Speed Vac Concentrator available from Savant Instruments, Inc., located at Farmingdale, NY, 11735. Then the tube 101 can be placed in the holder 102.

Any protein can be obtained and used in the process of the present invention. Small proteins defined as having a molecular weight of less than or equal to 10,000, middle sized proteins defined as having a molecular weight of X where $10,000 < X \leq 50,000$, and large proteins having a molecular weight of greater than 50,000 have been found to be hydrolyzed by the present invention. Proteins used in the examples described herein include glucagon, bovine serum albumin and β-lactoglobulin A. Any protein can be hydrolyzed by use of the present invention including representative examples identified in Enzyme Nomenclature, Academic Press, Inc., 1979.

Preferably, a dry sample of proteins in the range of about 0.05 nanomoles to about 5 nanomoles is located in the tube 101. More preferably, a dry sample in the range of about 0.1 nanomoles to about 2 nanomoles is located in the tube 101.

Second, the dried protein sample in the tube 101 is flushed with a gas that will not react with the sample. Illustrative gases may include argon gas or nitrogen gas.

Third, an aqueous acidic solution is prepared and placed in the pyrolyzed tube 101 pyrolyzed either before or after the dried proteins are located in the tube 101. If added after, then the aqueous acidic solution is separately purged as described below.

The aqueous acidic solution comprises an aqueous solution of at least one acid. Representative examples of the solution can include solutions of hydrochloric acid, trifluoroacetic acid, proprionic acid, mercaptoethane sulfonic acid, methane sulfonic acid, any strong mineral acid (e.g., sulfuric acid) or mixtures thereof. Generally, the acid concentration may vary and the preferred acid concentration may vary significantly depending on the acid used. Preferably, the acidic solution is about 6 N hydrochloric aqueous acid solution. The solution may optionally include an antioxidant, 2-mercaptoethanol, mercaptoacetic acid, or phenol in an amount, such as 0.4%, of the total solution by volume. However, preferably an antioxidant is not included. Examples 4 and 5 show that near amounts of labile amino acids including methonine (MET), serine (SER) and threonine (THR) are recovered using the present invention without the solution including an antioxidant.

The aqueous acidic solution can be flushed, for example by placing about one to about five milliliters of the acid in a separate container or tube and then purging the solution by bubbling it with nitrogen gas for about five minutes or more.

Preferably, about 0.100 to about 0.5 milliliters of the purged solution is placed in the tube 101. More preferably, about 0.100 to about 0.150 milliliters of the solution is placed in the tube 101. The solution can be pipetted into the tube 101.

Fourth, after the dried protein sample and the solution are in the tube 101 and the tube 101 is in the holder 102, then (1) the inside of the tube 101 is flushed with a gas as described above, (2) the septum 103 is placed over the holder and tube surface or edges, 112 and 107, respectively, and (3) the cap 104 is screwed over the septum 103 onto the holder 102 to seal the apparatus 100.

The sealed apparatus 100 can be irradiated with microwaves, such as by being placed in a microwave oven and heated for a period of time until a desired percent of conversion from proteins to amino acids is accomplished.

Protein hydrolysis is time and temperature dependent. The longer the sample is heated, the more of the sample that is converted until it is entirely amino acids. Different proteins hydrolyze at different temperatures and take different time periods to hydrolyze.

Protein hydrolysis according to the process of the present invention completes after about 25 minutes to about 40 minutes.

Protein samples will hydrolyze when exposed to microwave energy in a commercially available microwave oven rated at 700 watts at a setting of 80% for the duration of exposure. However, this wattage has not yet been determined to be critical. Samples described herein were exposed to about 700 watts of microwave energy for 80% of the time which is at a setting of 80% of full power for the microwave oven used. Any microwave oven can be used. The experiments described herein used a Whirlpool microwave oven, Model MW3500XM, available from Whirlpool Corporation with offices at Benton Harbor, MI, 49022. Although different microwave ovens may have the same power rating, they may not perform identically and some variation in times and power levels may be required to effect hydrolysis.

Following the above procedure, the sealed apparatus 100 contains its sample without leakage throughout the hydrolysis.

After heating, the sealed apparatus 100 can be removed from the oven and allowed to cool to room temperature. The glass tube 101 is removed from the holder and its contents are evaporated to dryness by any suitable means, such as by use of the aforementioned Speed Vac Concentrator. The resulting residue is redissolved in a buffer solution, such as Na-S buffer solution available from Beckman Instruments, Inc. of Fullerton, CA, 92634 which contains 4 nanomoles of norleucine to act as an internal standard. Any buffer solution can be used to redissolve the residue as long as the solution is compatable with the chromatography used in the analyzing instrument.

From an analysis of the residues dissolved in the buffer, the amino acid compositions of the protein sample can be determined using, for instance, a 6300 Beckman Aminoacid-Ninhydrin Analyzer available from Beckman Instruments, Inc., of Fullerton, CA 92634.

Using the aforedescribed procedure, one can recover about 60 percent or more of the constituent amino acids. The mean recovery of at least six protein samples is about 70% or more, where the mean recovery is calculated using the following formula:

$$X = \frac{X_1 + X_2 + \ldots + X_n}{n}$$

where e,ovs/X/ = mean or average
n = number of samples
$X_1$ = 1st sample value
$X_n$ = nth sample value.

Furthermore, the residues per mole for each constituent amino acid for at least six protein samples are within a standard deviation (Dev.) of plus or minus about 5 residues per mole of actual or published standard values for the amino acids in specified proteins, where the standard deviation is calculated using the following formula:

$$\sigma = \frac{\sqrt{\Sigma X^2 - nX^2}}{n}$$

where
$\sigma$ = standard deviation
$\Sigma = X_1 + X_2 + \ldots X_n$
$X_1$ 1st sample value
$X_n$ nth sample value
n = number of samples
e,ovs/X/ = mean or average.

Preferably, a plurality of the protein samples dissolved in aqueous acid solutions are prepared and sealed in apparatuses 100 according to the aforesaid procedure. Referring again to FIG. 3, the plurality of sealed apparatus 100 are evenly distributed in holes 130 in and around the apparatus support 132.

The apparatus support 132 is then placed in a microwave oven on the device 134 for slowly rotating the support 132 to provide even heating of the samples in the microwave oven. Empty apparatuses 100 can be placed in the support 132 so that weight is generally evenly distributed on the rotatable device 134.

The process of this invention is further illustrated by the following examples, wherein all temperatures are expressed in degrees Celsius (° C.) and all percentages are by weight unless otherwise indicated.

EXAMPLE 1

Six aliquots, each containing 100 "protein(s)' is intended and defined to include microliters(μL) of a solution containing 2 nanomoles of glucagon having a molecular weight of 3483, were carefully placed in the bottom of different replaceable nonpyrolyzable tubes 101. The samples were evaporated to dryness by means of a Speed Vac Concentrator. The tubes 101 were then placed in holder bodies 102 and thoroughly flushed with argon.

A quantity of 5 milliliters (mL) of 6 N hydrochloric acid containing 0.4% by weight of 2-mercaptoethanol in a separate container was purged and degassed with nitrogen. While being purged, an aliquot of 100 μL of the hydrochloric acid was pipetted into each tube 101 containing the protein sample and a self-sealing septum 116 from Waters Associates, Milford, MA 01757 was placed over the top of each of the tubes 101. Then caps 122 were quickly and tightly screwed on over the septums 116 onto the holders 106.

The six sample containing apparatuses 100 plus one empty apparatus 100 were placed in holes 130 of a holder support 132. The support 132 had 14 holes evenly distributed around it. Thus, an apparatus 100 was located in every other hole 130.

The support 132 with the seven apparatuses 100 were placed on a rotatable device 134 in a Whirlpool microwave oven, Model MW3500XM. The samples were heated for 30 minutes at a setting of 80% of full power, or 560 watts of microwave energy.

After heating, the support 132 and apparatuses 100 were removed and allowed to cool to room temperature. The tubes 101 were then removed and their contents evaporated to dryness by means of the Speed Vac Concentrator. The resulting residues were dissolved in 100 μL of sample dilution buffer (Na-S buffer, Beckman Instruments, Inc., Fullerton, CA 92634) which contains 4 nanomoles of norleucine to act as an internal standard.

Then 50 μL aliquots of each sample was analyzed. Specifically, the amino acid compositions of each hydrolyzed sample were determined with a 6300 Beckman Aminoacid-Ninhydrin Analyzer. The results of the analysis are shown in Table 1. Further, Table 1 shows published values for glucagon (STD) which were obtained using the conventional Hirs et al. method of protein hydrolysis. Published standard (STD) values for proteins used in the Examples described herein can be found in the Atlas of Protein Sequence and Structure, Volume 5, pages 208-319 (1972) and Volume 5, Supplement 2, page 267 (1976).

This Example 1 demonstrates that a small protein (i.e., protein having a molecular weight less than or equal to 10,000) is hydrolyzed effectively by the present invention. This Example 1 shows that the recovered residues per mole (or, alternatively, the recovered number of molecules of the amino acid per the number of molecules of the protein in the sample) for each constituent amino acid including labile amino acids (i.e., THR, SER, MET and HIS) are within a standard deviation (Dev.) of plus or minus 0.15 residues per mole of the published standard (STD) values. Further, this Example 1 shows a mean recovery of 82.6% of the protein sample for six samples which is comparable to recoveries generally obtained hydrolyzing proteins using the process disclosed in Hirs et al.

TABLE 1

| Amino Acid | STD | Residues per Mole | | | | | | mean | Dev. |
| --- | --- | --- | --- | --- | --- | --- | --- | --- | --- |
| | | 1 | 2 | 3 | 4 | 5 | 6 | | |
| Asx | 4 | 4.29 | 4.02 | 4.16 | 4.03 | 4.12 | 4.18 | 4.13 | 0.09 |
| THR | 3 | 2.99 | 2.88 | 2.89 | 2.79 | 2.90 | 2.92 | 2.90 | 0.06 |
| SER | 4 | 3.95 | 3.77 | 3.66 | 3.63 | 3.72 | 3.76 | 3.75 | 0.10 |
| GLX | 3 | 2.95 | 3.00 | 3.01 | 2.95 | 3.03 | 3.01 | 2.99 | 0.03 |
| PRO | 0 | | | | | | | | |
| GLY | 1 | 1.13 | 1.15 | 1.11 | 1.20 | 1.12 | 1.10 | 1.14 | 0.03 |
| ALA | 1 | 1.06 | 1.06 | 1.05 | 1.04 | 1.07 | 1.05 | 1.06 | 0.01 |
| VAL | 1 | 0.71 | 0.82 | 0.91 | 0.88 | 0.91 | 0.88 | 0.85 | 0.07 |
| MET | 1 | 1.00 | 0.92 | 1.00 | 0.99 | 1.00 | 1.02 | 0.99 | 0.03 |

TABLE 1-continued

| Amino Acid | STD | Residues per Mole | | | | | | mean | Dev. |
|---|---|---|---|---|---|---|---|---|---|
| | | 1 | 2 | 3 | 4 | 5 | 6 | | |
| ILE | 0 | | | | | | | | |
| LEU | 2 | 1.91 | 1.98 | 1.96 | 1.93 | 1.96 | 1.94 | 1.95 | 0.02 |
| TYR | 2 | 2.03 | 2.01 | 2.05 | 1.96 | 1.98 | 1.99 | 2.00 | 0.03 |
| PHE | 2 | 1.81 | 1.89 | 1.93 | 1.87 | 1.89 | 1.89 | 1.88 | 0.04 |
| HIS | 1 | 0.97 | 0.97 | 0.96 | 1.35 | 0.93 | 0.95 | 1.02 | 0.15 |
| LYS | 1 | 1.01 | 1.17 | 0.99 | 1.06 | 1.03 | 1.00 | 1.04 | 0.06 |
| ARG | 2 | 2.20 | 2.26 | 2.19 | 2.20 | 2.25 | 2.23 | 2.22 | 0.03 |
| % Recovery | | 82.0 | 76.4 | 87.2 | 85.6 | 84.4 | 80.1 | 82.6 | 4.4 |

EXAMPLE 2

Six aliquots, each 50 μL of an aqueous solution, each containing 0.1 nanomoles of bovine serum albumin having a molecular weight of 68,000 were prepared and hydrolyzed as in Example 1 for 30 minutes and analyzed. The published amino acid composition for bovine serum albumin (ST) and that obtained for each of the six samples is shown in Table 2.

This Example 2 demonstrates that a large protein (i.e., a protein having a molecular weight greater than 50,000) is effectively hydrolyzed by the present invention. Like Example 1, Example 2 shows that the recovered residues per mole for each constituent amino acid including the labile ones are very close to the published STD values. The residues per mole for each amino acid are within a standard deviation (Dev.) of plus or minus 4.27 residues per mole of the published STD values. Example 2 shows a mean recovery of 91.5% for the six samples which is comparable to recoveries generally obtained hydrolyzing proteins using the process disclosed in Hirs et al.

TABLE 2

| Amino Acid | STD | Residues per Mole | | | | | | mean | Dev. |
|---|---|---|---|---|---|---|---|---|---|
| | | 1 | 2 | 3 | 4 | 5 | 6 | | |
| Asx | 53 | 54.3 | 57.6 | 53.8 | 52.7 | 57.5 | 57.0 | 55.48 | 1.95 |
| THR | 34 | 28.1 | 32.3 | 31.7 | 31.4 | 29.7 | 31.0 | 30.70 | 1.41 |
| SER | 28 | 17.6 | 27.7 | 26.3 | 26.0 | 28.2 | 27.7 | 25.58 | 3.66 |
| GLX | 80 | 79.7 | 78.0 | 78.6 | 78.0 | 80.3 | 79.7 | 79.05 | 0.90 |
| PRO | 28 | 39.4 | 50.3 | 49.0 | 50.3 | 52.1 | 51.2 | 48.72 | 4.27 |
| GLY | 16 | 19.2 | 18.2 | 17.8 | 19.3 | 19.3 | 18.53 | 18.53 | 0.54 |
| ALA | 46 | 46.3 | 45.6 | 46.0 | 46.1 | 49.2 | 49.4 | 47.10 | 1.57 |
| VAL | 36 | 35.8 | 26.4 | 30.1 | 30.9 | 25.5 | 26.6 | 29.22 | 3.55 |
| MET | 4 | 3.4 | 3.8 | 3.7 | 3.7 | 4.0 | 4.0 | 3.77 | 0.21 |
| ILE | 14 | 12.9 | 9.8 | 11.1 | 11.5 | 9.1 | 9.5 | 10.65 | 1.32 |
| LEU | 61 | 60.7 | 56.5 | 58.2 | 59.5 | 57.2 | 56.6 | 58.12 | 1.55 |
| TYR | 19 | 19.6 | 19.1 | 19.2 | 19.7 | 19.3 | 19.1 | 19.33 | 0.24 |
| PHE | 27 | 27.0 | 25.0 | 25.7 | 26.1 | 25.5 | 25.2 | 25.75 | 0.66 |
| HIS | 17 | 17.2 | 16.5 | 16.3 | 14.5 | 14.2 | 16.0 | 15.78 | 1.08 |
| LYS | 59 | 58.0 | 58.1 | 55.8 | 55.2 | 55.0 | 54.3 | 56.07 | 1.47 |
| ARG | 23 | 25.0 | 23.3 | 24.4 | 24.7 | 24.1 | 24.0 | 24.25 | 0.54 |
| ARG | 23 | 25.0 | 23.3 | 24.4 | 24.7 | 24.1 | 24.0 | 24.25 | 0.54 |
| % Recovery | | 95.1 | 89.1 | 94.7 | 95.3 | 85.3 | 89.3 | 91.5 | 3.80 |

EXAMPLE 3

Six aliquots, each 50 μL of an aqueous solution, each containing 1.0 nanomole of β-lactoglobulin A having a molecular weight of 18,281 were hydrolyzed as in Example 1 for 30 minutes and analyzed The published amino acid composition of β-lactoglobulin (STD) and that obtained for each of the six samples is shown in Table 3.

This Example 3 demonstrates that a middle size protein (i.e., a protein having a molecular weight of X, where 10,000 < X ≦ 50,000 is effectively hydrolyzed by the present invention. Here, the recovered residues per mole for each amino acid including the labile ones are within a standard deviation (Dev.) of plus or minus 1.26 residues per mole of the published STD values. Here, the mean recovery is 92.3% for six samples which again is comparable to recoveries generally obtained hydrolyzing proteins under the Hirs et al. process.

TABLE 3

| Amino Acid | STD | Residues per Mole | | | | | | mean | Dev. |
|---|---|---|---|---|---|---|---|---|---|
| | | 1 | 2 | 3 | 4 | 5 | 6 | | |
| Asx | 15 | 15.8 | 16.2 | 16.2 | 16.3 | 15.1 | 16.0 | 15.93 | 0.40 |
| THR | 8 | 7.8 | 8.1 | 7.9 | 8.0 | 7.5 | 8.0 | 7.9 | 0.20 |
| SER | 7 | 6.3 | 7.0 | 6.7 | 7.0 | 6.6 | 6.9 | 6.7 | 0.24 |
| GLX | 25 | 25.4 | 26.0 | 25.8 | 25.9 | 25.5 | 25.8 | 26.2 | 1.26 |
| PRO | 8 | 10.9 | 11.8 | 11.8 | 11.6 | 11.7 | 11.7 | 11.6 | 0.32 |
| GLY | 4 | 3.2 | 3.3 | 3.2 | 3.5 | 3.3 | 3.2 | 3.3 | 0.11 |
| ALA | 15 | 14.4 | 15.0 | 14.7 | 14.9 | 14.9 | 14.9 | 14.8 | 0.20 |
| VAL | 9 | 9.4 | 8.4 | 8.8 | 8.3 | 8.7 | 8.3 | 8.7 | 0.38 |
| MET | 4 | 3.7 | 3.9 | 3.8 | 3.9 | 4.0 | 3.6 | 3.8 | 0.13 |

TABLE 3-continued

| Amino Acid | STD | Residues per Mole | | | | | | mean | Dev. |
|---|---|---|---|---|---|---|---|---|---|
| | | 1 | 2 | 3 | 4 | 5 | 6 | | |
| ILE | 10 | 8.6 | 7.7 | 7.9 | 7.6 | 8.0 | 7.8 | 7.9 | 0.33 |
| LEU | 22 | 21.9 | 21.8 | 21.7 | 21.6 | 22.4 | 22.2 | 22.0 | 0.29 |
| TYR | 4 | 4.0 | 3.9 | 3.9 | 3.8 | 4.0 | 3.9 | 3.9 | 0.06 |
| PHE | 4 | 4.0 | 3.9 | 3.9 | 3.9 | 4.0 | 3.9 | 3.9 | 0.05 |
| HIS | 2 | 1.7 | 1.6 | 1.6 | 1.8 | 1.6 | 1.7 | 1.7 | 0.08 |
| LYS | 15 | 14.6 | 14.2 | 14.4 | 14.4 | 14.8 | 14.6 | 14.5 | 0.20 |
| ARG | 3 | 3.2 | 2.8 | 2.9 | 2.8 | 3.0 | 2.8 | 2.9 | 0.13 |
| % Recovery | | 107.5 | 106.6 | 78.9 | 84.0 | 83.0 | 93.8 | 92.3 | 11.7 |

EXAMPLE 4

Twelve aliquots, each 50 μL of an aqueous solution, each containing 0.5 nanomoles of β-lactoglobulin A were hydrolyzed for 30 minutes as in Example 1 except that no 2-mercaptoethanol was present. The published amino acid composition of β-lactoglobulin (STD) and that obtained for each of the twelve samples is shown in Table 4.

This Example 4 when compared to Example 3 demonstrates that although an antioxidant, such as 2-mercaptoethanol, may be present in the acidic solution as in Example 3, an antioxidant is not required to protect labile amino acids. Specifically, the standard deviation of recovered THR from its published value is significantly less without an antioxidant (i.e., 0.08) in comparison to with an antioxidant (i.e., 0.20). Whereas, the standard deviations for SER, MET and HIS are very comparable regardless of the presence of an antioxidant. Note that an antioxidant is required to protect (i.e., recover) labile amino acids under the Hirs et al. process.

TABLE 4

| Amino Acid | STD | Residues per Mole | | | | | | | | | | | | mean | Dev. |
|---|---|---|---|---|---|---|---|---|---|---|---|---|---|---|---|
| | | 1 | 2 | 3 | 4 | 5 | 6 | 7 | 8 | 9 | 10 | 11 | 12 | | |
| Asx | 15 | 17.2 | 17.1 | 16.2 | 17.6 | 17.4 | 17.6 | 16.8 | 17.1 | 18.2 | 16.9 | 16.9 | 16.8 | 17.14 | 0.29 |
| THR | 8 | 8.2 | 8.2 | 6.6 | 8.2 | 8.2 | 8.1 | 8.1 | 8.2 | 7.7 | 8.0 | 8.1 | 8.0 | 8.1 | 0.08 |
| SER | 7 | 7.4 | 7.2 | 4.8 | 7.6 | 7.7 | 7.7 | 7.4 | 8.1 | 7.7 | 7.2 | 7.1 | 7.0 | 7.3 | 0.25 |
| GLX | 25 | 26.9 | 26.5 | 25.8 | 26.9 | 27.0 | 27.0 | 26.3 | 26.7 | 27.4 | 26.6 | 26.3 | 26.2 | 26.6 | 0.29 |
| PRO | 8 | 8.6 | 8.6 | 8.5 | 8.8 | 8.5 | 8.9 | 8.5 | 8.6 | 9.0 | 8.6 | 8.5 | 8.5 | 8.6 | 0.13 |
| GLY | 4 | 3.6 | 3.4 | 3.7 | 3.6 | 3.9 | 3.6 | 3.4 | 3.6 | 4.0 | 3.4 | 3.4 | 3.4 | 3.5 | 0.16 |
| ALA | 15 | 15.7 | 15.5 | 14.6 | 16.2 | 16.1 | 16.4 | 15.3 | 15.6 | 17.3 | 15.5 | 15.3 | 15.0 | 15.7 | 0.42 |
| VAL | 9 | 7.8 | 8.0 | 10.2 | 7.1 | 7.3 | 7.1 | 8.3 | 7.7 | 6.2 | 8.3 | 8.1 | 8.4 | 7.8 | 0.47 |
| MET | 4 | 3.8 | 3.7 | 2.5 | 4.0 | 3.7 | 4.1 | 3.6 | 3.8 | 4.4 | 3.7 | 3.7 | 3.5 | 3.8 | 0.17 |
| ILE | 10 | 7.2 | 7.6 | 9.6 | 6.9 | 6.7 | 6.8 | 7.8 | 7.4 | 6.3 | 7.8 | 7.7 | 7.8 | 7.4 | 0.42 |
| LEU | 22 | 22.4 | 22.5 | 22.9 | 22.4 | 22.2 | 22.4 | 22.6 | 22.4 | 22.6 | 22.6 | 22.4 | 22.4 | 22.4 | 0.11 |
| TYR | 4 | 3.6 | 3.8 | 3.8 | 3.7 | 3.6 | 3.7 | 3.8 | 3.8 | 3.7 | 3.8 | 3.7 | 3.8 | 3.7 | 0.08 |
| PHE | 4 | 3.9 | 3.9 | 4.2 | 3.9 | 3.8 | 3.9 | 3.8 | 3.8 | 3.7 | 3.8 | 3.7 | 3.8 | 3.7 | 0.06 |
| HIS | 2 | 1.7 | 1.6 | 2.2 | 1.5 | 1.7 | 1.4 | 1.7 | 1.6 | 1.4 | 1.6 | 1.7 | 1.7 | 1.6 | 0.10 |
| LYS | 15 | 15.8 | 15.0 | 15.4 | 14.7 | 15.2 | 14.5 | 15.2 | 14.9 | 14.7 | 15.2 | 15.4 | 15.5 | 15.1 | 0.36 |
| ARG | 3 | 2.5 | 2.6 | 3.2 | 2.3 | 2.5 | 2.3 | 2.6 | 2.6 | 1.4 | 2.1 | 2.6 | 2.7 | 2.5 | 0.18 |
| % Recovery | | 73.5 | 74.3 | 82.6 | 74.6 | 79.1 | 67.8 | 74.4 | 72.4 | 60.7 | 74.6 | 77.8 | 82.2 | 75.1 | 3.7 |

EXAMPLE 5

Twelve aliquots, each 50 μL of a solution, each containing 0.1 nanomoles of bovine serum albumin were hydrolyzed for 30 minutes as in Example 1 except that no 2-mercaptoethanol was present. The published amino acid composition of bovine serum albumin (STD) and that obtained for each of the twelve samples is shown in Table 5.

This Example 5 when compared to Example 2 demonstrates that improved proline (PRO) recovery values are obtained by omitting an antioxidant from the acidic solution.

TABLE 5

| Amino Acid | STD | Residues per Mole | | | | | | | | | | | | mean | Dev. |
|---|---|---|---|---|---|---|---|---|---|---|---|---|---|---|---|
| | | 1 | 2 | 3 | 4 | 5 | 6 | 7 | 8 | 9 | 10 | 11 | 12 | | |
| Asx | 53 | 55.5 | 56.1 | 56.4 | 55.8 | 53.8 | 54.9 | 54.9 | 58.7 | 55.2 | 54.2 | 54.3 | 55.5 | 55.28 | 0.69 |
| THR | 34 | 32.2 | 32.4 | 32.2 | 32.1 | 30.7 | 32.2 | 32.1 | 31.7 | 32.2 | 31.8 | 31.9 | 32.1 | 32.12 | 0.16 |
| SER | 28 | 27.3 | 27.8 | 28.0 | 27.7 | 24.3 | 26.7 | 26.7 | 30.4 | 27.2 | 26.4 | 26.6 | 27.6 | 27.20 | 0.54 |
| GLX | 80 | 81.3 | 81.5 | 82.0 | 81.2 | 80.0 | 80.8 | 81.1 | 83.3 | 81.4 | 80.4 | 80.4 | 81.4 | 81.15 | 0.47 |
| PRO | 28 | 28.9 | 28.8 | 29.2 | 29.6 | 27.9 | 28.2 | 28.5 | 28.3 | 30.0 | 28.6 | 28.1 | 28.9 | 28.88 | 0.56 |
| GLY | 16 | 17.1 | 17.5 | 17.4 | 17.3 | 16.8 | 17.8 | 17.0 | 21.9 | 17.2 | 17.0 | 17.0 | 17.3 | 17.26 | 0.25 |
| ALA | 46 | 48.9 | 49.3 | 49.2 | 49.1 | 48.0 | 48.3 | 48.5 | 51.1 | 48.9 | 49.2 | 48.4 | 49.0 | 48.78 | 0.38 |
| VAL | 36 | 31.0 | 30.5 | 29.4 | 29.8 | 34.9 | 32.0 | 32.5 | 27.2 | 31.2 | 32.3 | 31.9 | 30.2 | 31.08 | 1.03 |
| MET | 4 | 3.7 | 3.5 | 3.9 | 3.7 | 3.0 | 3.5 | 3.5 | 3.1 | 3.7 | 2.9 | 3.5 | 3.8 | 3.57 | 0.26 |
| ILE | 14 | 12.1 | 11.9 | 11.6 | 11.6 | 13.7 | 12.5 | 12.7 | 9.7 | 12.2 | 12.7 | 12.4 | 11.7 | 12.14 | 0.41 |
| LEU | 61 | 61.4 | 61.5 | 61.0 | 60.8 | 62.7 | 61.9 | 62.2 | 59.1 | 62.0 | 61.8 | 61.7 | 61.3 | 61.56 | 0.42 |
| TYR | 19 | 18.3 | 18.2 | 18.4 | 18.2 | 17.8 | 18.3 | 18.3 | 17.6 | 18.5 | 18.1 | 18.3 | 18.4 | 18.30 | 0.11 |
| PHE | 27 | 27.0 | 27.0 | 26.9 | 26.8 | 27.6 | 27.2 | 27.4 | 26.3 | 27.3 | 27.2 | 27.1 | 27.1 | 27.10 | 0.64 |
| HIS | 17 | 17.2 | 17.3 | 16.8 | 18.7 | 18.5 | 17.5 | 16.7 | 16.1 | 15.6 | 18.6 | 19.1 | 18.1 | 17.56 | 1.02 |

TABLE 5-continued

| Amino Acid | STD | Residues per Mole | | | | | | | | | | | | mean | Dev. |
|---|---|---|---|---|---|---|---|---|---|---|---|---|---|---|---|
| | | 1 | 2 | 3 | 4 | 5 | 6 | 7 | 8 | 9 | 10 | 11 | 12 | | |
| LYS | 59 | 59.2 | 58.6 | 59.1 | 59.6 | 60.4 | 59.2 | 59.0 | 60.4 | 59.0 | 59.9 | 59.7 | 58.8 | 59.11 | 0.40 |
| ARG | 23 | 24.0 | 23.9 | 23.8 | 24.1 | 24.0 | 24.1 | 24.0 | 24.1 | 24.1 | 24.4 | 23.9 | 23.9 | 24.02 | 0.17 |
| % Recovery | | 85.5 | 83.4 | 77.6 | 84.8 | 89.8 | 89.5 | 83.7 | 82.0 | 81.7 | 84.6 | 86.1 | 83.6 | 84.02 | 2.90 |

COMPARATIVE EXAMPLE A

A Teflon®vial similar to the one described in the Chen et al. article was made. The vial comprised a Teflon®body, a disk-shaped silicon septum, and a Teflon®cap. The body had a base wall connected to a cylindrical wall which ended in a male portion having machine threads. In other words, the threaded portion was not tapered. The cap comprised a flat wall for contacting the septum, the flat wall connected to a cylindrical female pipe non-tapered machine threaded portion for threadably engaging the male threaded portion of the body. The vial enclosed a space that could contain up to and no more than 2 milliliters of sample.

An amount of 0.200 nanamoles of bovine serum albumin dissolved in 0.1 N hydrochloric acid was introduced into the vial. The sample was dried in a Speed-Vac Concentrator. An amount of 100 microliters of 6 N hydrochloric acid with 0.4% 1-mercaptoethanol purged with nitrogen gas was introduced into the vial. The vial was then purged with argon gas and the septum and cap were tightly affixed thereon. The vial was placed in the microwave oven and exposed to about 700 watts of microwave energy for 80% of seven minutes. Then the vial was removed from the oven and cooled. The resultant solution was dried in the Speed Vac. The dried constituent of the vial was redissolved in 100 microliters (μL) of pH 2.2 buffer containing norleucine as an internal standard. An amount of 50 microliters of this solution was injected onto the Beckman 6300 amino acid analyzer. The results of the analysis indicated that no amino acids were recovered.

COMPARATIVE EXAMPLE B

Comparative Example A was repeated, except the threaded portion of the vial body and cap had pipe threads. In other words, the threaded portion of the vial body and the corresponding threaded portion of the cap were tapered. The analysis results similarly indicated that no amino acids were recovered.

COMPARATIVE EXAMPLE C

An amount of 2.0 nanamoles of bovine serum albumin in an aqueous solution was introduced into a glass test tube. The sample was dried in a Speed-Vac Concentrator. A solution of hydrochloric acid and mercaptoethanol was introduced into the tube. The tube was purged with argon while being placed in an upright position in a Teflon®jar. The jar was then sealed closed with a cap. The jar was placed in the microwave oven and exposed to full power or about 700 watts of microwave energy for 20 minutes. Then the jar was removed from the oven, cooled and opened. Residue had dried inside the tube and on the inside jar walls. Analysis of the residue through use of the Beckman 6300 showed that amino acids were present. However, due to the residue on the jar walls, a meaningful quantitative analysis of the residue could not be performed.

Comparative Example C is provided to show that not just any apparatus can be used to hold a protein sample during microwave hydrolysis and reslut in a residue that is capable of convenient and meaningful quantitative analysis. Further, it showed that complete hydrolysis had not occurred under the conditions provided.

COMPARATIVE EXAMPLE D

Comparative Example C was repeated, except that while the jar and its contents were being exposed to microwaves for less than one (1) minute, fumes permeated the lab from the oven. The experiment was immediately stopped.

Comparative Example D is provided to show that not all apparatuses can withstand the heat and pressures generated by microwave hydrolysis so as to maintain a protein sample sealed within the apparatus throughout the process.

COMPARATIVE EXAMPLE E

A sample of bovine serum albumin dissolved in an aqueous acidic solution was introduced into a pyrolyzed glass tube sealed within a Teflon®holder screwed to a Teflon®cap. A septum was located between the holder and cap. The apparatus was microwaved for 7 minutes at 100% power, i.e., about 700 watts. After heating, the apparatus was cooled and then opened. Most of the residue was condensed on the inside walls of the holder. Analysis of some of the residue by use of the Beckman 6300 indicated that partial hydrolysis occurred.

Comparative Example E shows that not all apparatuses comprising a septum and a cap adequately seal a protein sample within the tube during microwave hydrolysis.

COMPARATIVE EXAMPLE F

A sample of bovine serum albumin dissolved in an aqueous acidic solution was introduced into a pyrolyzed tube. Then the tube was placed in a Teflon®vial. A septum was placed on the exposed tube end. Then a cap was screwed onto the vial enclosing the septum and tube. The apparatus was microwaved for 7 minutes at full power. The apparatus did not retain all of the sample and solution. Some leaked out. Analysis of some of the residue retained in the tube indicated that partial hydrolysis was achieved.

Comparative Example F shows that not all apparatuses adequately seal a protein sample within the apparatus throughout microwave hydrolysis.

What is claimed is:

1. An apparatus for holding a sample of proteins dissolved in an aqueous acidic solution while the sample is being irradiated with microwaves to produce constituent amino acids from the proteins, the apparatus comprising:

a tube including a nonpyrolyzable glass body enclosing an inner space for holding proteins dissolved in a solution, the body having a substantially flat surface with an opening to the inner space;

a holder including a body having an outer threaded portion ending with a lip, an inner chamber defined by an inner wall substantially the shape of and for holding the tube, and a substantially flat surface connected to the lip, the substantially flat holder surface having a hole leading to the holder inner chamber, such that the tube can be inserted into the hole where the tube rests on the inner chamber wall and the substantially flat tube surface is substantially parallel to and slightly extended from the substantially flat holder surface;

a disk-shaped septum having a side for contacting the substantially flat surfaces of the tube and the holder such that when the side of the disk is contacting the substantially flat tube and holder surfaces, the disk extends slightly beyond the lip; and a cap including an inner threaded portion connected to an inner wall, such that the inner threaded portion of the cap screws onto the outer threaded portion of the holder compressing the septum between the cap inner wall and the substantially flat tube and holder surfaces sealing the apparatus when holding a sample of proteins dissolved in a solution being irradiated with microwaves.

2. The apparatus of claim 1, further comprising:
an apparatus support having a plurality of holes for inserting a plurality of the holders.

3. The apparatus of claim 2, further comprising:
means for slowly rotating the apparatus support.

4. The apparatus of claim 1, wherein the volume of the tube comprises no more than 0.5 milliliters.

* * * * *